(12) United States Patent
Chevalet et al.

(10) Patent No.: US 6,844,169 B1
(45) Date of Patent: Jan. 18, 2005

(54) CONSTRUCTS FOR CONTROLLED EXPRESSION OF RECOMBINANT PROTEINS IN PROKARYOTIC CELLS

(75) Inventors: Laurent Chevalet, Annemasse (FR); Alain Robert, Annemasse (FR); Jean-Yves Bonnefoy, Le Sappey (FR); Thien Ngoc Nguyen, Saint Julien en Genevois (FR)

(73) Assignee: Pierre Fabre Medicament, Castres Cedex (FR)

( * ) Notice: Subject to any disclaimer, the term of this patent is extended or adjusted under 35 U.S.C. 154(b) by 0 days.

(21) Appl. No.: 09/673,288

(22) PCT Filed: Apr. 14, 1999

(86) PCT No.: PCT/FR99/00874
§ 371 (c)(1),
(2), (4) Date: Dec. 7, 2000

(87) PCT Pub. No.: WO99/53080
PCT Pub. Date: Oct. 21, 1999

(30) Foreign Application Priority Data

Apr. 14, 1998 (FR) .............................. 98 04638

(51) Int. Cl.⁷ .......................... C12P 21/06; C12P 21/04; C12N 1/20; C12N 15/74
(52) U.S. Cl. ................... 435/69.1; 435/71.1; 435/71.2; 435/488; 435/252.33
(58) Field of Search .............................. 435/69.1, 71.1, 435/71.2, 488, 252.33

(56) References Cited

U.S. PATENT DOCUMENTS 5,416,008 A    5/1995   Bailey

FOREIGN PATENT DOCUMENTS

EP      298 207 A     11/1988

OTHER PUBLICATIONS

Warne et al. Use of a modified Escherichia cole trpR gene to obtain tight regulation iof high–copy–number expression vectors Gene 46 1986 103–112.*
Yanofsky et al. Some novel transcription attenuation mechanisms used by bacteria Biochimie 1996 78, 1017–1024.*
Kamath, et al. Characterization of the Tryptophanase Operon of *Proteus vulgaris*. (1992) The Journal of Biological Chemistry 267:19978–85.
Phillips, et al. Evidence That Cysteine 298 Is in the Active Site of Tryptophan Indole–Iyase (1989) The Journal of Biological Chemistry 264:10627–32.
Yansura, D. et al., "Use of *Escherica coli* trp promoter for direct expression of proteins", Methods in Enzymology, vol. 185, pp 54–60, 1990.
Yanofsky, C. et al., "Some novel trnascription attenuation mechanisms used by bacteria", Biochime, vol. 78, No. 11–12, pp 1017–1024, 1996.
Warne, S. et al., "Use of a modified *Escherichia coli* trpR gene to obtain tight regulation of high–copy–No. expression vectors", GENE, vol. 46, pp 103–112, 1986.

* cited by examiner

*Primary Examiner*—James Ketter
*Assistant Examiner*—Konstantina Katcheves
(74) *Attorney, Agent, or Firm*—The Firm of Mueschen and Sage (57) ABSTRACT

The invention concerns a novel construct for expressing a gene coding for a recombinant protein of interest placed under the control of the Ptrp tryptophan operon promoter in a procaryotic host cell. The invention is characterised in that the construct comprises a nucleic sequence capable of inactivating the gene coding for a TnaA tryptophanase when said nucleic sequence is introduced in said host cell. The invention also concerns vectors containing said construct and host cells transformed by said vectors. The invention further concerns methods for producing said recombinant proteins using said novel constructs.

21 Claims, 4 Drawing Sheets

CONSTRUCTS FOR CONTROLLED EXPRESSION OF RECOMBINANT PROTEINS IN PROKARYOTIC CELLS

The invention comprises a novel construct for expressing a gene encoding a recombinant protein of interest placed under the control of the Ptrp tryptophan operon promoter in a prokaryotic host cell, characterized in that the construct comprises a nucleic acid sequence which is capable of inactivating the gene encoding a TnaA tryptophanase when said nucleic acid sequence is introduced into said host cell, vectors containing said construct and the host cells transformed with said vectors. A subject of the invention is also the methods for producing said recombinant proteins using these novel constructs.

The present invention is generally used for producing recombinant polypeptides or proteins by so-called recombinant DNA methods. More particularly, the present invention relates to the production of recombinant polypeptides or proteins by transformed host cells which are bacterial in type, and in which expression is directed by or is under the control of the Ptrp tryptophan operon promoter/operator (Nichols & Yanofsky, 1983).

*Escherichia coli* (*E. coli*) is the most commonly used and best characterized organism for the purpose of production of recombinant proteins. Various expression systems are used in *E. coli* and, among them, the Ptrp tryptophan operon promoter is considered to be one of the strongest (Yansura & Bass, 1997).

However, not all recombinant genes are expressed with the same effectiveness by *E. coli*. It has been described and observed that the accumulation of a recombinant protein produced during the culturing of transformed host cells can rapidly lead to plasmid instability, a decrease in, or even an arrest of, cell growth, and a decrease in the overall yield of recombinant product. In this case, it is important to have available a system of controlled and regulated expression which makes it possible to divide the production process into two phases; a first so-called cell growth phase in which the activity of the promoter is minimal, followed by a so-called induction or derepression phase which favors the expression and accumulation of the recombinant protein.

Ptrp, the tryptophan operon promoter of *E. coli*, is suitable for producing recombinant proteins because of its inducible nature. Repression at the level of the Ptrp operator is carried out by the product of the trpR regulatory gene, when this product, which is also named trp aporepressor, is bound to tryptophan (corepressor). Absence of tryptophan renders the TrpR protein incapable of binding to the operator, thus causing a derepression of the tryptophan operon. Diverse examples of expression of heterologous genes under the control of Ptrp show that the leaking of expression therefrom is too great to allow the production, under satisfactory conditions, of recombinant proteins, in particular those which are toxic for the cell (Yansura and Henner, 1990).

The TrpR regulatory protein is subjected to a self-regulation mechanism (Kelley & Yanofsky, 1982), and its concentration tends toward a mean value of 120 molecules per *E. coli* K-12 cell, in the presence of an excess of exogenous tryptophan (Gunsalus, Gunsalus Miguel & Gunsalus, 1986). This concentration, while it is sufficient to regulate correctly the activity of the single Ptrp chromosomal promoter, may prove to be limiting in the face of several tens of vectors containing the same promoter. With regard to tryptophan, it may also be a limiting factor even if it is provided in excess in the culture medium. In *E. coli*, there is, in fact, a tryptophanase activity which is encoded by the tnaA gene, and which is capable of degrading tryptophan to indole, thus diverting it from its regulatory function (Snell, 1975). In addition, tryptophanase can be induced by tryptophan, which makes any attempt to compensate this degradation phenomenon with an increase in the supply of tryptophan pointless.

Various approaches directed towards obtaining the best possible control of leaking of expression have been envisaged and described. However, some have the drawback of only being applicable on a laboratory scale (Hasan & Szybalski, 1995; Suter-Crazzolara & Unsicker, 1995), or of decreasing the yield of recombinant product (Stark, 1987).

Consequently, there is, today, a great need to develop a system of controlled expression of recombinant proteins of interest which can be used on a large scale and which makes it possible, in particular, to control leaking of expression. This is precisely the subject of the present invention.

The invention relates to novel constructs based on the Ptrp expression system, which, when they are introduced into a prokaryotic host cell, preferably of bacterial type, make it possible to decrease the residual expression of recombinant genes at the start of culturing, these novel constructs providing improved control of the synthesis of recombinant proteins.

A subject of the present invention is a construct for expressing a gene encoding a recombinant protein of interest placed under the control of the Ptrp tryptophan operon promoter in a prokaryotic host cell, characterized in that the construct comprises a nucleic acid sequence which is capable of inactivating the gene encoding a TnaA tryptophanase when said nucleic acid sequence is introduced into said host cell.

The expression "recombinant protein of interest" is intended to refer to all proteins, polypeptides or peptides which are obtained by genetic recombination, which can be used in fields such as human or animal health, cosmetology, human or animal nutrition, the agroindustry or the chemical industry. Among these proteins of interest mention may be made in particular, but without being limited thereto, of:

a cytokine and in particular an interleukin, an interferon, a tissue necrosis factor and a growth factor, and in particular a hematopoietic growth factor (G-CSF, GM-CSF), a hormone such as human growth hormone or insulin, a neuropeptide, a factor or cofactor involved in clotting and in particular factor VIII, von Willebrand factor, antithrombin III, protein C, thrombin and hirudin, an enzyme and in particular trypsin, a ribonuclease and β-galactosidase, an enzyme inhibitor such as α1-anti-trypsin and viral protease inhibitors, a protein capable of inhibiting the initiation or progression of cancers, such as the expression products of tumor suppressor genes, for example the P53 gene, a protein capable of stimulating an immune response or an antibody, such as for example the proteins, or their active fragments, of the external membrane of a Gram-negative bacterium, in particular the OmpA proteins of Klebsiella or human respiratory syncytial virus protein G, a protein capable of inhibiting a viral infection or its development, for example the antigenic epitopes of the virus in question or modified variants of viral proteins which can compete with native viral proteins, a protein which can be contained in a cosmetic composition, such as substance P or a superoxide dismutase, a dietary protein,
an enzyme capable of directing the synthesis of chemical or biological compounds, or capable of degrading certain toxic chemical compounds, or alternatively
any protein which is toxic with respect to the microorganism which produces it, in particular if this microorganism is the bacterium *E. coli*, such as for example, but without being limited thereto, the protease of the HIV-1 virus, the protein ECP (ECP for Eosinophil Cationic Protein) or the 2B and 3B proteins of poliovirus.

The expression "nucleic acid sequence capable of inactivating the gene encoding a TnaA tryptophanase when said nucleic acid sequence is introduced into said host cell" is intended to refer to a nucleic acid sequence capable of modifying said gene in such a way that this modification leads to the loss of tryptophanase activity of said host cell, the product of expression of said modified gene being incapable of degrading tryptophan to indole and thus diverting it from its regulatory function. Among said nucleic acid sequences capable of inactivating the gene coding for a TnaA tryptophanase when one of said nucleic acid sequences is introduced into said host cell, a nucleic acid sequence encoding an inactivated TnaA tryptophanase obtained by mutation, such as by substitution, insertion and/or deletion of at least one nucleotide of the nucleic acid sequence encoding an active TnaA tryptophanase, is preferred.

The invention comprises a construct according to the invention, characterized in that the prokaryotic host cell is a Gram-negative bacterium, preferably belonging to the *E. coli* species.

The invention also relates to a construct according to the invention, characterized in that it also comprises, upstream of said nucleic acid sequence capable of inactivating the gene encoding a TnaA tryptophanase when said nucleic acid sequence is introduced into said host cell, all or part of the nucleic acid sequence of the Ptna tryptophanase operon promoter.

Preferably, the invention relates to a construct according to the invention, characterized in that said nucleic acid sequence capable of inactivating the gene encoding a TnaA tryptophanase when said nucleic acid sequence is introduced into said host cell comprises a mutated fragment of the coding sequence of said TnaA tryptophanase.

Preferably, the invention relates to a construct according to the invention, characterized in that said mutated fragment is obtained by inserting a stop codon at a position such that the sequence of the mutated fragment thus obtained encodes a protein fragment lacking tryptophanase activity.

Just as preferably, the invention relates to a construct according to the invention, characterized in that said mutated fragment is a mutated fragment of the coding sequence of the TnaA tryptophanase of said host cell.

With regard to the nucleic acid sequence encoding the TnaA tryptophanase of *E. coli*, and to its Ptna promoter, reference will be made in the present description to the sequence published by Deeley and Yanofsky (1981).

With regard to the nucleic acid sequences encoding the Ptrp tryptophan operon promoter/operator, reference will be made to the sequence published by Yanofsky et al. (1981).

The invention also relates to a construct according to the invention, characterized in that said nucleic acid sequence capable of inactivating the gene encoding a TnaA tryptophanase when said nucleic acid sequence is introduced into said host cell comprises a nucleic acid sequence comprising all or part of the sequence of a promoter which is followed, in the 3' position, by a nucleic acid sequence encoding a molecule which is ribonucleotide or protein in nature, and which acts negatively on the Ptrp promoter.

Preferably, the invention relates to a construct according to the invention, characterized in that said promoter which is followed, in the 3' position, by a nucleic acid sequence encoding a molecule which is ribonucleotide or protein in nature, and which acts negatively on the Ptrp promoter, is all or part of the Ptna tryptophanase operon promoter of *E. coli*.

Equally preferably, the invention comprises a construct according to the invention, characterized in that said nucleic acid sequence encoding a molecule which is ribonucleotide or protein in nature, and which acts negatively on the Ptrp promoter, is the sequence encoding the TrpR tryptophan operon aporepressor of *E. coli* or one of its biologically active fragments such as the one described by Gunsalus and Yanofsky (1980).

The expression "a nucleic acid sequence comprising all or part of the sequence of a promoter" is intended to refer to a nucleic acid sequence comprising all the sequence of a promoter, or one of its biologically active fragments, which is capable of directing or of controlling the expression of a gene which is functionally linked to it.

In the present description, the expression "biologically active fragment of a promoter" will be intended to refer to any sequence of a fragment of said promoter, which fragment is capable of directing or of 0.1 controlling the expression of the gene which is located downstream of said fragment, said gene being functionally linked to said fragment.

In the present description, the expression "biologically active fragment of the TrpR tryptophan operon aporepressor" will be intended to refer to any fragment of said aporepressor which has conserved its repressor activity.

The expression "nucleic acid sequence encoding a molecule which is ribonucleotide in nature, and which acts negatively on the Ptrp promoter", the preferred ribonucleotides are those chosen from the following sequences:

a) 5'-AUUCGCGUCU ACGGCUUCAU CGUGUUGCGC-3' (SE ID NO. 1)

b) 5'-AUUCGCGUCU ACGGCUUCAU CGUGUUGCGC AGCACAACGC GCCUGUCACC GGAUGUGUUU UCCGGUCUGA UGAGUCCGUG AGGACGAAAC AGG-3' (SEQ ID NO. 2)

c) 5'-AUUCAGUACG AAAAUUGCUU UCAUAAUUCU AGAUACCCUU UUUACGUGAA CUU-3' (SEQ ID NO. 3)

d) 5'-AUUCAGUACG AAAAUUGCUU UCAUAAUUCU AGAUACCCUU UUUACGUGAA CUUAGCACAAi CGCGCCUGUC ACCGGAUGUG UUUUCCGGUC UGAUGAGUCC GUGAGGACGA AACAGG-3' (SEQ ID NO. 4)

e) 5'-AUUCGCGUCU ACGGCUUCAU CGUGUUGCGC AUUCAGUACG AAAAUUGCUU UCAUAAUUCU AGAUACCCUU UUUACGUGAA CUU-3 (SEQ ID NO. 5)

f) 5'. AUUCGCGUCU ACGGCUUCAU CGUGUUGCGC AUUCAGUACG AAAAUUGCUU UCAUAAUUCU AGAUACCCUU UUUACGUGAA CUUAGCACAA CGCGCCUGUC ACCGGAUGUG UUUUCCGGUC UGAUGAGUCC GUGAGGACGA AACAGG-3' (SEQ ID NO. 6)

g) 5'-CUUCGCGUCC UGAUGAGUCC GUGAGGACGA AACGGCUUCC-3' (SEQ ID NO. 7)

h) 5-CUUCGCGUCC UGAUGAGUCC GUGAGGACGA AACGGCUUCC AGCACAACGC GCCU-

GUCACC GGAUGUGUUU UCCGGUCUGA UGAGUCCGUG AGGACGAAAC AGG-3'. (SEQ ID NO. 8)

Another aspect of the invention relates to a vector containing a construct according to the invention.

Preferably, the vector according to the invention is characterized in that it is the vector pMAK705[tnaAt] or the vector PMAK705[Ptna::trpR::3'tna].

The invention also relates to a prokaryotic host cell, preferably a bacterium of the *E. coli* species, transformed with a vector according to the invention.

In another aspect, a subject of the invention is a method for producing recombinant protein in a host cell using a construct according to the invention A subject of the invention is also a method for producing a recombinant protein of interest according to the invention, in which said construct is introduced into the DNA of the prokaryotic host cell.

Preference is given to a method for producing recombinant proteins according to the invention, in which said construct is introduced into the DNA of the prokaryotic host cell with a vector according to the invention, preferably according to the chromosomal integration method described in Example 1 or 2.

A subject of the invention is also a method for producing recombinant proteins according to the invention, in which said construct is introduced without any other DNA element which would allow a selective advantage to be associated therewith.

Preferably, the invention comprises a method for producing a recombinant protein of interest according to the invention, in which said construct is introduced at the tryptophanase operon locus of *E. coli*, preferably at the tna gene locus, and better still at the tnaA gene locus.

Preference is given to a method for producing recombinant proteins of interest according to the invention, characterized in that it comprises the following steps:

a) transforming a prokaryotic cell with a vector according to the invention, and integrating said construct into the DNA of said host cell;

b) transforming said prokaryotic cell with a vector containing a gene encoding said recombinant protein of interest;

c) culturing said transformed cell in a culture medium which allows the expression of the recombinant protein; and d) recovering the recombinant protein from the culture medium or from said transformed cell.

A subject of the invention is also a method for producing recombinant proteins of interest according to the invention, characterized in that said method also comprises, between step a) and b) of the above method, a resolution and a screening step.

The invention also relates to a method for producing recombinant proteins of interest according to the invention, in which control of the expression of the recombinant proteins before induction of the Ptrp promoter is obtained by inducing said promoter which is followed, in the 3' position, by a nucleic acid sequence encoding a molecule which is ribonucleotide or protein in nature, and which acts negatively on the Ptrp promoter according to the invention.

Finally, the invention also comprises a production method according to the invention, in which the induction of said promoter which is followed, in the 3' position, by a nucleic acid sequence encoding a molecule which is ribonucleotide or protein in nature, and which acts negatively on the Ptrp promoter according to the invention, is obtained by any means enabling an inhibitory or activating effect to be exerted on said promoter.

Preferably, the invention comprises a production method according to the invention, in which the induction of said promoter which is followed, in the 3' position, by a nucleic acid sequence encoding a molecule which is ribonucleotide or protein in nature, and which acts negatively on the Ptrp promoter according to the invention, is obtained either:

a) by choosing a suitable carbon source in the culture medium; or b) by adding tryptophan to the culture medium; or by a combination of a) and b).

The construct and vector systems, the prokaryotic host cells transformed with said vectors and the methods of the invention which are described above and which will be exemplified in the examples hereinbelow fall within the context of controlling the production of recombinant proteins in prokaryotic cells. They are suitable for the expression of homologous or heterologous genes placed downstream of the Ptrp promoter/operator. Two mutants are more particularly described below in order to illustrate the invention. They bear the names ICONE 100 and ICONE 200 (ICONE for Improved Cells for Over- and Non-leaky Expression). The modifications introduced into the ICONE line have the following characteristics:

1) they are integrated into the host's chromosome, 2) since they are generated using a site-directed mutagenesis technique, they are targeted to a single site in the bacterial DNA, this site being completely known since it is the tna operon located at 83 min on the physical map of the *E. coli* K-12 genome. In this respect, the consequences for the host from a physiological point of view are fully identified. In particular, the possibility that cryptic functions are reactivated following the chromosomal integration, as is suspected in the case of random mutagenesis, is ruled out, 3) the technology used in these examples for the chromosomal integration (Hamilton et al. (1989)) excludes the possibility that other sequences are inserted into the bacterial DNA. In particular, the mutants do not carry any genes for resistance to an antibiotic. Should they be used on an industrial scale, they offer the producer and the legislator the guarantee that they will have no selective advantage in the event of accidental dissemination in the environment.

According to one aspect of the invention, a first type of mutant or transformed cell named ICONE 100 is described, which carries a mutation in the tnaA gene, leading to a loss of tryptophanase activity. The phenotype associated with this mutation is an absence of tryptophan degradation. This type of mutant, after transformation with a reporter vector and culturing on a medium which conventionally promotes tryptophanase activity, turns out to be superior to the isolate from which it is derived in terms of control of repression by tryptophan.

According to another aspect of the invention, a second type of mutant named ICONE 200 is described, which carries a cassette for expressing the trpR gene under the control of the Ptna tryptophanase promoter, integrated at the tnaA gene locus. The use of the tna locus as a target for the integration leads, in the host bacterium, to a loss of tryptophanase activity, which causes, as described above, an inability to convert tryptophan to indole. Moreover, the presence of the Ptna::trpR cassette in the chromosome confers on this novel trpR gene the characteristics of Ptna, i.e. sensitivity to catabolic repression (Isaacs, Chao, Yanofsky, & Saier, 1994; Botsford & DeMoss, 1971) and inducibility by tryptophan (Stewart & Yanofsky, 1985). The latter property constitutes an innovation in which the plasmid Ptrp promoter is controlled, at the level of transcription, by a chromosomal promoter, Ptna, which is antagonistic to it. Surprisingly, after transformation with an expression vector and culturing in a fermenter, ICONE 200 turns out to be superior to the isolate from which it is derived in terms of control of repression by tryptophan.

The bacteria which have one of the characteristics mentioned above are useful for the controlled production of recombinant molecules thus, a subject of the present invention is also the use of said transformed bacteria in a method for producing recombinant proteins.

In the examples below, the advantage provided by the two mutants is clearly demonstrated using *Escherichia coli* β-galactosidase as the recombinant protein.

Another aspect of the invention lies in the characteristics of the mutations introduced. They are fully defined, controlled from a genetic and biochemical point of view, targeted to the tna locus of *E. coli*, and free of a selection marker.

The mutant or transformed microorganisms of the invention are constructed using prokaryotes, more precisely Gram-negative bacteria belonging to the *Escherichia coli* species. The properties of the tryptophanase operon promoter of *E. coli* (which can be induced by tryptophan, sensitive to catabolic repression) were used to direct the transient synthesis of a mediator which acts negatively on Ptrp-directed expression. However, it is known that other bacterial species, in particular those which colonize the intestinal tract of animals, are capable of synthesizing a tryptophanase which can be induced by tryptophan (Snell. 1975). Consequently, other strains than *E. coli* are suitable for carrying out the methods described and for producing recombinant proteins therein.

The examples and figures which follow are intended to illustrate the invention without in any way limiting the scope thereof.

LEGENDS OF THE FIGURES

FIG. 2: Kinetics of β-gal activity of the strains RV308, ICONE 100 and ICONE 200×pVA-βgal.
The bacteria transformed with a vector containing the β-galactosidase gene under the control of the Ptrp promoter are cultured in a fermenter. The β-galactosidase activity is measured by incubating a cell extract in the presence of ONPG (β-galactosidase-specific substrate).

FIG. 4A: RV308×pVA-polio2B
FIG. 4B: ICONE 200×pVA-polio2B
FIG. 5: Analysis by SDS-PAGE of the polio-2B protein purified by nickel affinity chromatography.
A: Experiment No. 2: induction with 5 µg/ml of IAA when the optical density is equal to 32.5;
B: Experiment No. 1: induction with 25 µg/ml of IAA when the optical density is equal to 32.5;
C: Experiment No. 4: induction with 5 µg/ml of IAA when the optical density is equal to 63.5;
D: Experiment No. 3: induction with 25 µg/ml of IAA when the optical density is equal to 62.5;
MW: molecular weight marker (kDa).

The invention is based on the stable introduction of mutations into the genome of the host strain. All the modifications given in the examples below are introduced at the tna locus of *E. coli*, consisting schematically of the following series:
A) Ptna promoter,
B) coding sequence of tnaA (tryptophanase) gene,
C) intergenic region,
D) coding sequence of the tnaB (tryptophan permease) gene,
E) transcription terminator.

More specifically, the modifications relate to element (B). This is replaced to the benefit of an element (b), the characteristics of which in the diverse constructs are as follows:

TABLE 1

Nature of the mutations carried by ICONE 100 and ICONE 200

| Mutant name | Nature of element (b) |
| --- | --- |
| ICONE 100 | Coding sequence of tnaA interrupted at position +221 by a stop codon and an XbaI restriction site |
| ICONE 200 | Coding sequence of the trpR gene encoding the Ptrp aporepressor |

EXAMPLE 1

Construction of the Mutant ICONE 100

A DNA fragment, marked tnaAT, is amplified by PCR. It stretches from position-275 to position +1054 with respect to the first nucleotide of the coding sequence of tnaA. This fragment, which overlaps Ptna promoter and tnaA, is amplified by two-part PCR reaction. Part I stretches from position-275 to position +220. It is amplified with the aid of the oligonucleotides Trp5 (sense) and Trp2 (antisense), the sequence of which is:

```
Trp5:      5'-CGGGATCCGTGTGACCTCAAAATGGT-3'      (SEQ ID NO. 9)
              BamHI

Trp2:      3'-CTACGCGCCGCTGCTTCGGATTAGATCTCG-5'  (SEQ ID NO. 10)
(antisense)                          stop XbaI
```

Part II is located in the coding sequence of tnaA, immediately 3' of part I. It stretches from position +221 to position +1054. It is amplified with the aid of the oligonucleotides Trp3 and Trp4:

```
Trp3:      5'-CGTCTAGACAGCGGCAGTCGTAGCTAC-3'     (SEQ ID NO. 11)
              XbaI

Trp4:      3'-CCTTCTCTAACCGCAACAGTTCGAACG-5'     (SEQ ID NO. 12)
(antisense)                    HindIII
```

The PCR reactions are carried out using as a matrix *E. coli* K-12 colonies lyzed in the Taq polymerase buffer (AmpliTaq Gold CETUS, USA).

The amplification products are precipitated with ethanol, and then digested with the suitable restriction enzymes (BamHI/XbaI for part I, XbaI/HindIII for part II). An analysis on agarose gel stained with ETB makes it possible to verify that the fragments have the expected size (Deeley C Yanofsky, 1981). The tnaAT fragment is generated by ligating the two fragments I and II at the XbaI site. It differs from the natural sequence by the presence of a stop codon at position +221, followed by an XbaI restriction site. This tnaAT fragment is cloned into the vector pRIT28 (Hultman, Stahl, Hornes & Uhlen, 1989), at the BamHI/HindIII sites, and sequenced. The tnaAT fragment is subcloned into the vector pMAK705 (Hamilton, Aldea, Washburn, Babitzke & Kushner, 1989), giving pMAK705[tnaAT].

The method used to generate a genetic rearrangement in *E. coli* is the one described by Hamilton et al. (1989). It is based on the use of the suicide vector pMAK705, which carries a heat-sensitive origin of replication which is functional at 30° C. but inactive beyond 42° C., and the chloramphenicol (CMP) resistance gene. *E. coli* RV308 (Maurer, Meyer & Ptashne, 1980) is transformed with 4 μg of vector pMAK705 [tnaAT], and the transformation mixture is plated out on plates containing LB medium +20 μg/ml CMP. After overnight incubation at 30° C., three clones are subcultured in LB liquid medium +20 μg/ml CMP and incubated at 30° C. with stirring until an OD at 580 nm close to 1 is reached. The suspensions are then plated out on LB medium +20 μg/ml CMP and incubated at 44° C. and at 30° C. The colonies which develop at 44° C. (=co-integrants) are carrying a chromosomal integration of the vector, this integration being promoted by the existence of sequence homologies between the chromosome and the insert carried by the vector.

The so-called resolution phase consists in promoting the excision of the vector through a mechanism of recombination between repeated sequences present on the chromosome. Some clones isolated at 44° C. are cultured in LB liquid medium +20 μg/ml CMP at 30° C. for three days, renewing the medium regularly. The suspensions are then diluted, plated out on LB agar medium +20 μg/ml CMP, and incubated at 30° C. until separate colonies appear. Several tens of colonies are subcultured in duplicate on LB agar medium +20 μg/ml CMP at 30° C. and 44° C. The colonies which do not develop at 44° C. are selected and screened with a PCR reaction which indicates whether resolving the vector has conserved the stop codon and the XbaI site at the tna locus. The oligonucleotides used are Trp6 (sense) and Trp7 (antisense), which are homologous to the desired mutation and to a portion of the tnaA terminator, respectively:

```
Trp6:      5'-CGACGAAGCCTAATCTAGA-3'     (SEQ ID NO. 13)
                          stop XbaI Trp7:      3'-CCGATATTCCTACAATCGG-5'     (SEQ ID NO. 14)
(antisense)
```

Out of eighteen screened clones, nine give an amplification fragment with the expected size indicating the presence of the stop codon followed by the XbaI site in the tnaA gene. The other nine clones do not give an amplification product, probably because the resolution step has restored on the chromosome the unmutated tnaA gene. Among the nine positive clones, four are sampled and subjected to a clearing out of the plasmid by successive subculturing in the absence of selection pressure. After culturing for a few days, clones are obtained which have again become sensitive to chloramphenicol.

The presence of tnaA-inactivating mutation is confirmed in two different ways: firstly, a PCR amplification with the aid of the oligonucleotides Trp5 and Trp4, followed by a digestion with XbaI shows that the restriction site, which is absent in *E. coli* RV308, is present in the tnaA gene of the mutants; next, by culturing the mutants in a tryptophan-rich medium, followed by the indole test (adding the Kovacs reagent to the culture medium), it is shown that the mutants have not generated indole, whereas the strain RV308 of origin produces indole under the same conditions. It is deduced therefrom that the mutation introduced leads to a loss of tryptophanase activity.

One clone is selected for the purpose of conservation in frozen form. It is named ICONE 100.

EXAMPLE 2

Construction of the Mutant ICONE 200

A DNA fragment is constructed in vitro by PCR amplification of three subunits.

The first subunit located in the Ptna promoter stretches from position −511 to position +3 with respect to the first nucleotide of the coding sequence of tnaA. It is amplified using the oligonucleotides TrpR1 (biotinylated in the 5' position) and TrpR2:

```
TrpR1:        5'-CTGGATCCCTGTCAGATGCGCTTCGC-3'  (SEQ ID NO. 15)
                 BamHI

TrpR2:        3'-CTTCCTAATACATTACCGGGTTG-5'     (SEQ ID NO. 16)
(antisense)
```

The second subunit corresponds to the coding sequence of the trpR gene of E. coli. It is amplified using the oligonucleotides TrpR3 and TrpR4 (biotinylated in the 5' position):

```
TrpR3:        5'-GTAATGGCCCAACAATCACC-3'        (SEQ ID NO. 17)
                       start TrpR4:        3'-CACAACGACTTTTCGCTAACTGACGTCAG-5'  (SEQ ID NO. 18)
(antisense)                           PstI
```

The third subunit corresponds to the sequence located immediately 3' of the coding sequence of tnaA. It contains the intergenic region of the tna operon and a portion of the tnaB gene encoding tryptophan permease. It is amplified using the oligonucleotides TrpR5 and TrpR6:

```
TrpR5:        5'-CGCTGCAGTTAATACTACAGAGTGG-3'   (SEQ ID NO. 19)
                   PstI

TrpR6:        3'-CCAGCTAATGAGGTAAGTTCGAAC-5'    (SEQ ID NO. 20)
(antisense)                         HindIII
```

The amplified fragments are purified according to the GeneClean method (Bio101, Jolla, Calif., USA).

The subunits I and II are fused in the following way. In two separate tubes, each subunit is incubated with 30 µl of streptavidin-labeled beads (Dynabeads, DYNAL, Norway). After 20 min at 37° C. and 5 min at room temperature, the bound DNA is denatured with 50 µl of 0.15 M NaOH. The single-stranded DNAs recovered in each supernatant are mixed in equal parts and subjected to a hybridization reaction and an extension reaction in the presence of Taq polymerase (AmpliTaq Gold, CETUS, USA) according to five PCR cycles. The reaction product is amplified in a PCR reaction with the aid of the oligonucleotides TrpR1 and TrpR4.

The GeneClean-purified amplification product is digested with BamHI and PstI. The fragment thus isolated is cloned into the vector pRIT28 to give pRIT28[Ptna::trpR], and then sequenced.

The subunit III is digested with the enzymes PstI and HindIII, then cloned into pRIT28 to give pRIT28[3'tna], and then the sequence is verified by DNA sequencing (ABI 373A, Perkin Elmer, USA).

The vector pRIT28[Ptna::trpR] is digested with the enzymes PstI and HindIII, and then ligated in the presence of the subunit III, itself isolated from pRIT28[3'tna] by PstI/HindIII double digestion. The resulting vector is named pRIT28[Ptna::trpR::3'tna]. The insert is transferred into pMAK705 after double digestion with the enzymes 8 ml and HindIII The resulting plasmid is named pMAX705 [Ptna::trpR::3'tna].

The integration of the Ptna::trpR::3'tna fusion at the tna locus of E. coli RV308 is carried out under conditions similar to those described in Example 1. Briefly, the strain is transformed with the vector pMAX705[Ptna::trpR::3'tna], and then subjected to the integration and resolution steps.

The screening of the colonies at the end of resolution uses conditions which are slightly different to those in Example 1. The tna locus is amplified by PCR using the oligonucleotides TrpR11 and TrpR7:

TrpR 11: 5'-GGGCAGGTGAACTGCTGGCG-30 (SEQ ID NO. 21)

TrpR7: 3'-GGTGCCGTTATAAGGGTCGGAC-5'(SEQ ID NO. 22) (antisense)

TrpR11 hybridizes with the Ptna sequence upstream (5') of TrpR1, and TrpR7 hybridizes with the tnaB sequence downstream (3') of TrpR6. The amplification product has a different size depending on whether the gene placed downstream of Ptna is tnaA (situation encountered in RV308) or trpR (desired situation in the mutants). A colony which possesses trpR at the tna locus is conserved and named ICONE 200. An analysis of its chromosomal sequence shows that it possesses the trpR gene immediately downstream of the Ptna promoter. Culturing in the presence of tryptophan confirms the absence of indole formation, which is a logical consequence of the loss of the tnaA gene.

EXAMPLE 3

Leaking of Expression In the Presence of Succinate + Tryptophan

This example describes the relative capacities of E. coli RV308, ICONE 100 and ICONE 200 to control the expression of a recombinant protein under the control of the Ptrp promoter. To this effect, we constructed an expression vector termed pVA-βgal, in which the sequence encoding E. coli β-galactosidase is placed downstream of the Ptrp promoter. The vector of origin used for this construct is pVAABP308 (Murby, Samuelsson, Nguyen, et al., 1995).

Each of the three strains is transformed with the vector pVA-µgal. The transformants obtained are cultured individually in a complete medium (30 g/l Tryptic Soy Broth (DIFCO), 5 g/l Yeast Extract (DIFCO)) overnight at 37° C. An aliquot of these precultures is transferred into 60 ml of M9.YE.SUCC medium (1×M9 salt solution (DIFCO), 5 g/l Yeast Extract (DIFCO), 20 g/l sodium succinate). After an incubation time at 37° C. which allows the exponential growth phase to be reached, a sample is removed from each culture. The growth is estimated via the optical density at 580 nm of the bacterial suspension. The level of β-galactosidase activity is measured in each cell pellet. For this, 1 ml of culture is centrifuged for 3 min at 12 000 g. The cell pellet is taken up in 900 μl of buffer (50 mM Tris-HCl, pH 7.5/1 mM EDTA/100 mM NaCl/400 μg/ml lysozyme) and incubated for 15 min at 37° C. 100 μl of SDS (1% in 50 mM Tris-HCl, pH 7.5) are added, and the sample is placed at room temperature for 5 min. The assay is carried out by mixing 30 μl of sample, 204 μl of buffer (50 mM Tris-HCl, pH 7.5/1 mM $MgCl_2$) and 66 μl of ONPG (4 mg/ml in 50 mM Tris-HCl, pH 7.5). The reaction mixture is incubated at 37° C. The reaction is stopped by adding 500 μl of 1 M $Na_2CO_3$. The OD at 420 nm, related to the incubation time, is proportional to the β-galactosidase activity present in the sample. Since it is known that E. coli RV308 has a complete deletion of the 1 ac operon (Maurer, Meyer & Ptashne, 1980), the β-galactosidase activity assayed is only due to the expression of the gene carried by the vector pVA-βgal.

Table 2 summarizes the results obtained with each of the strains RV308, ICONE 100 and ICONE 200.

TABLE 2

Growth of the strains RV308, ICONE 100 and ICONE 200 and leaking of expression (mean and standard error over three experiments)

|  | OD 580 nm | β-GAL (U/ml) |
|---|---|---|
| RV308 | 2.47 ± 0.01 | 0.93 ± 0.09 |
| ICONE 100 | 3.69 ± 0.24 | 0.21 ± 0.03 |
| ICONE 200 | 2.43 ± 0.03 | 0.02 ± 0.00 |

The results in Table 2 show that the mutants of the ICONE line develop at least as well as the strain RV308 from which they are derived. The mutations introduced thus have no negative effect on growth. Moreover, the β-galactosidase activity measured is different in the three strains. ICONE 100 has an intracellular activity which is approximately 4.5 times lower than that of RV308. Under "succinate as carbon source" conditions, in which the activity of Ptna promoter is at a maximum (Botsford & DeMoss, 1971), the deletion of the tryptophanase gene thus leads to a decrease in leaking of expression, probably by limiting the degradation of the intracellular tryptophan (corepressor). Under the same conditions, the degree of leaking of expression in ICONE 200 is further decreased by 10-fold with respect to ICONE 100. The activity of the plasmid Ptrp promoter is thus at a minimum in ICONE 200. Firstly, the loss of the tryptophanase activity gives the bacterium the possibility of controlling Ptrp better, as is demonstrated for ICONE 100. However, ICONE 200 has a second property which distinguishes it from ICONE 100 in genetic terms and gives it, at the experimental level, a further advantage in terms of controlling expression. Thus, under conditions in which Ptna is active, ICONE 200 has the possibility of directing the overexpression of the TprR aporepressor, and, consequently, the leaking of expression measured at the level of the plasmid Ptrp promoter is decreased by a factor which is close to 50 with respect to the strain of origin RV308.

EXAMPLE 4

Leaking of Expression in the Presence of Glycerol +Tryptophan

This example demonstrates the advantage provided by the mutant ICONE 200 in a fermentation culture medium and under fermentation conditions which are close to those which might be used industrially for producing recombinant proteins with the Ptrp system.

Each of the three strains RV308, ICONE 100 and ICONE 200 is transformed with the vector pVA-βgal. The transformants obtained are cultured individually in 200 ml of complete medium (30 g/l Tryptic Soy Broth (DIFCO), 5 g/l Yeast Extract (DIFCO)) overnight at 37° C.

The cell suspension obtained is transferred sterilely to a fermenter (model CF3000 from Chemap, capacity 3.5 l) containing 1.8 liters of the following medium (concentrations for 2 liters of final culture): 90 g/l glycerol, 5 g/l (NH4)2SO$_4$, 6 g/l $KH_2PO_4$, 4 g/l $K_2HPO_4$, 9 g/l Na3-citrate.$2H_2O$, 2 g/l $MgSO_4.7H_{2O}$, 1 g/l yeast extract, 30 mg/l $CaCl_2.2H_2O$, 8 mg/l $ZnSO_4.7H_2O$, 7 mg/l $CoCl_2.6H_2O$, 7 mg/l $Na_2MoO_4.2H_2O$, 10 mg/l $MnSO_4.1H_2O$, 2 mg/l $H_3BO_3$, 8 mg/l $CuSO_4.5H_2O$, 54 mg/l $FeCl_3.6H_2O$, 0.06% antifoaming agent, 8 mg/i tetracycline and 200 mg/l tryptophan. The pH is regulated at 7.0 by adding aqueous ammonia. The dissolved oxygen content is maintained at 30% of saturation by automatically regulating the stirring speed and then the aeration flow rate, by measuring the dissolved $O_2$. When the optical density of the culture reaches a value between 40 and 45, the induction is carried out by adding 5 mg/l of indole acrylic acid (SIGMA).

Figure 1:
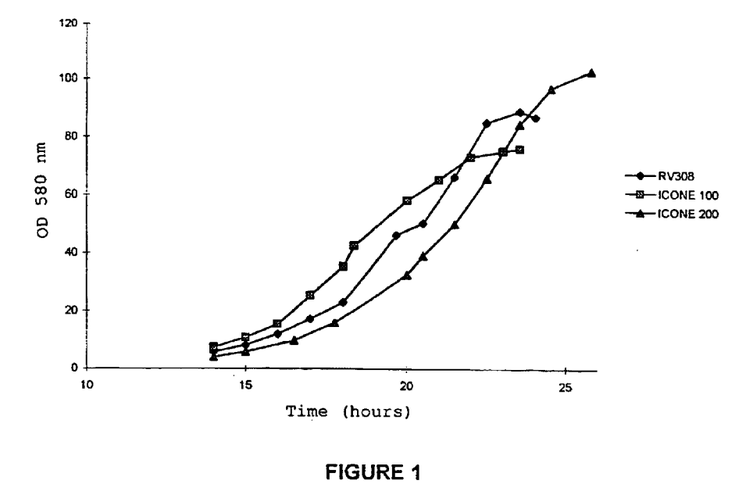
FIG. 1: Growth kinetics of the strains RV308, ICONE 100 and ICONE 200×pVA-βgal. OD 580 nm corresponds to the measurement of the optical density measured by spectrophotometry.
Figure 2:
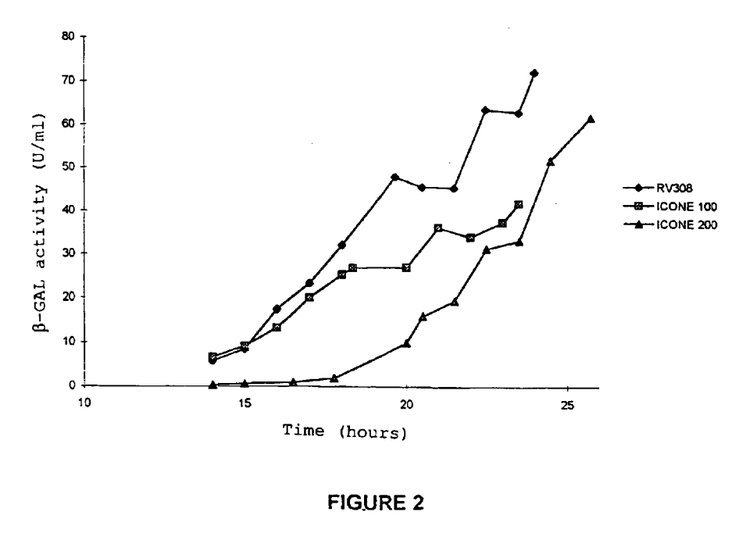
Figure 3:
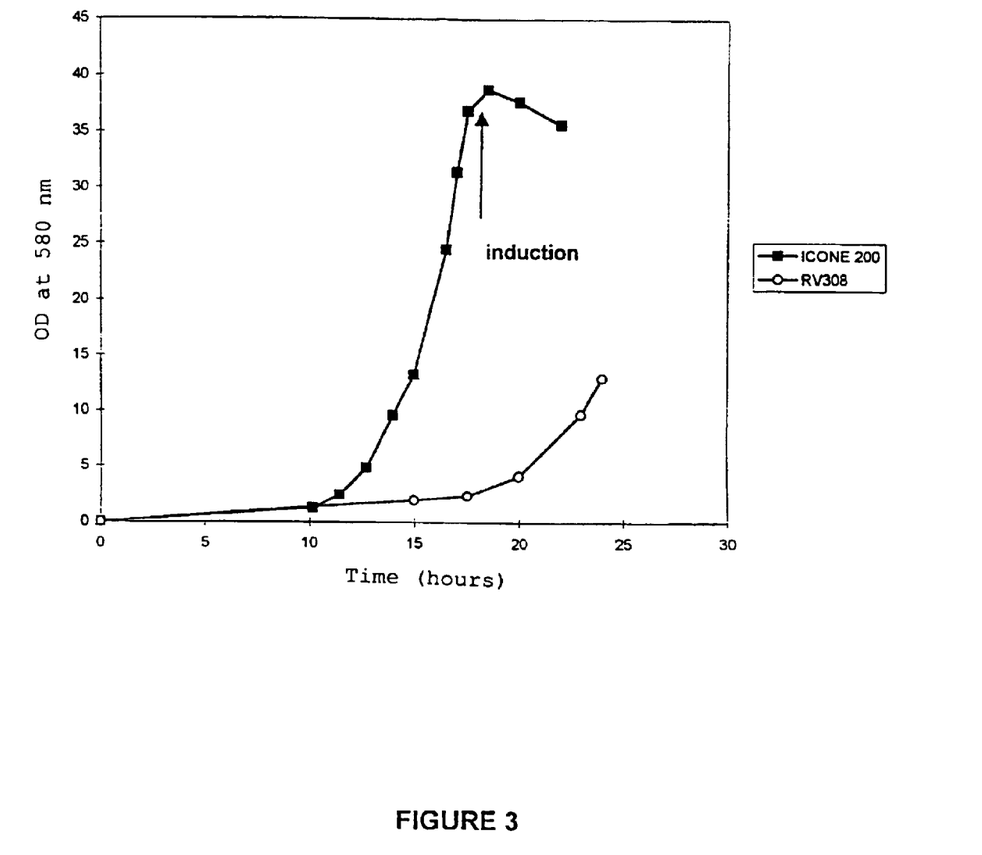
FIG. 3: Comparison of the growth kinetics of the *E. coli* strains RV308 and ICONE 200 transformed with the vector pVA-polio2B.
Figure 4A:
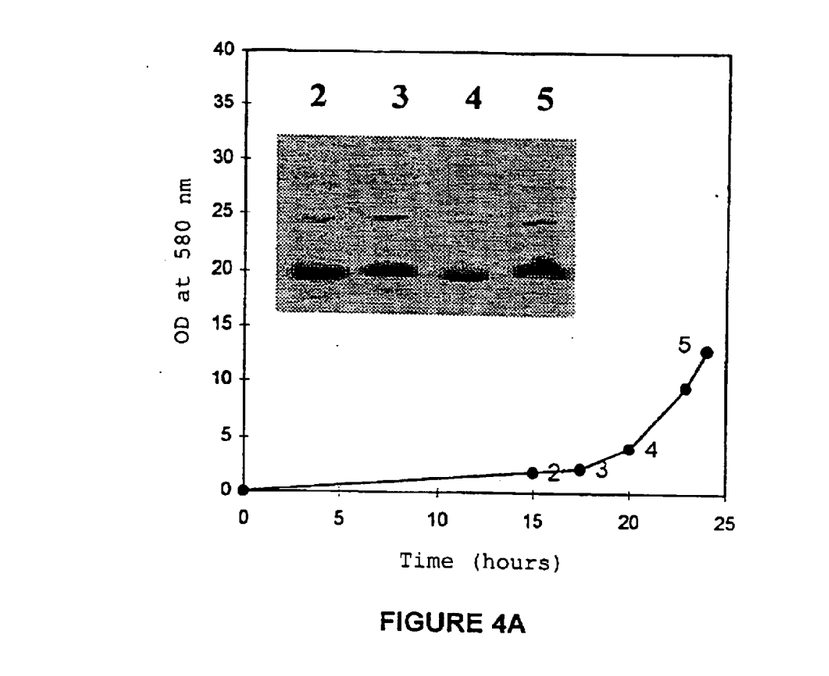
FIGS. 4A and 4B: Immunoblot on the intracellular extracts of the RV308 and ICONE 200 cultures transformed with the vector pVA-polio2B.
Figure 4B:
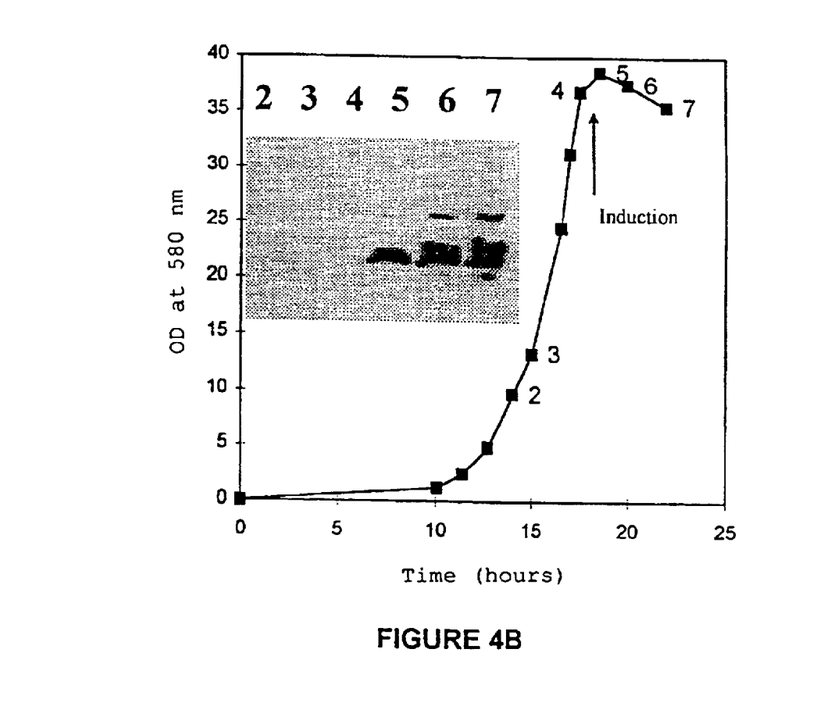
Figure 5:
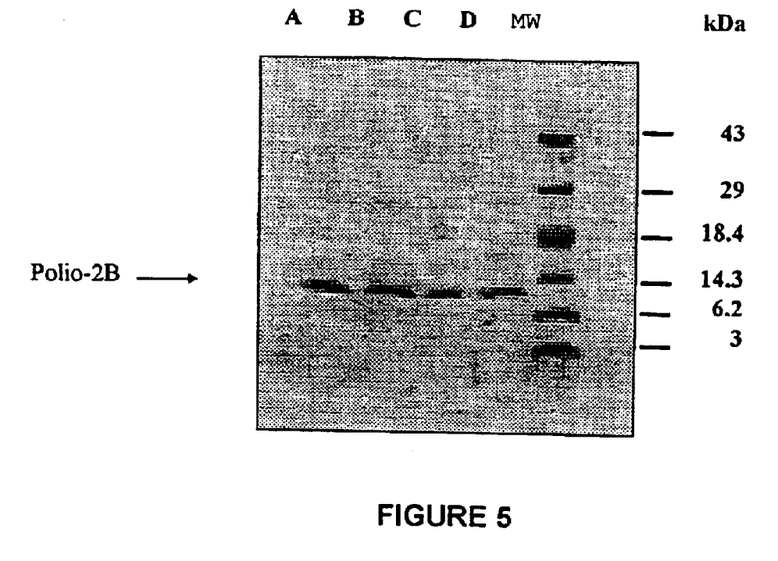
Figure 6:
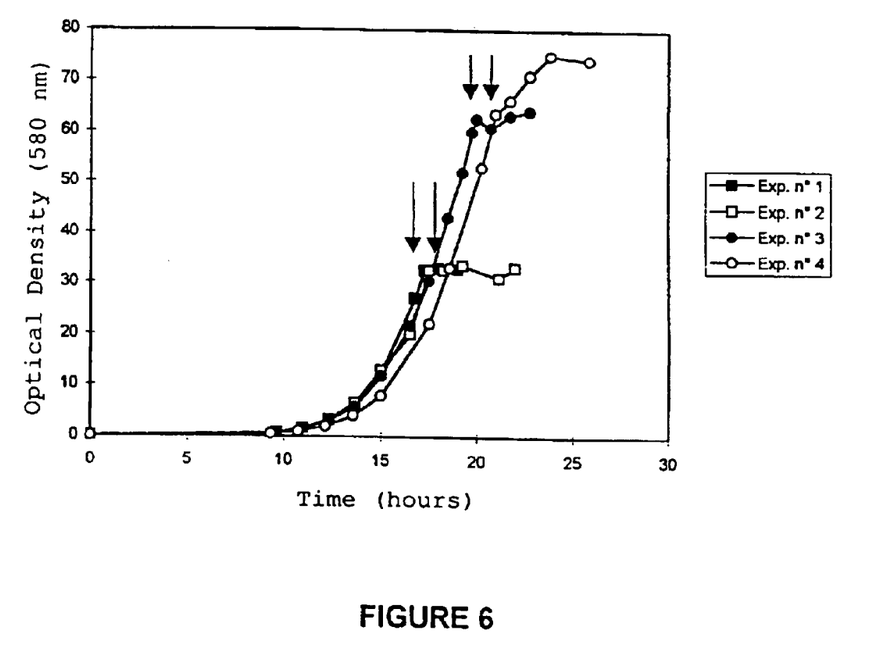
FIG. 6: Growth kinetics of ICONE 200×pVA-polio2B: influence of the induction time and of the inducer concentration.
■ Experiment No. 1: induction with 25 µg/ml of IAA when the optical density is equal to 32.5.
□ Experiment No. 2: induction with 5 µg/ml of IAA when the optical density is equal to 32.5.
● Experiment No. 3: induction with 25 µg/ml of IAA when the optical density is equal to 62.5.
○ Experiment No. 4: induction with 5 µg/ml of IAA when the optical density is equal to 63.5. The arrows indicate the moment of induction.

An analysis by kinetics of the optical density of the culture (OD at 580 nm of the suspension) and of the intracellular β-galactosidase activity (see Example 3) is carried out. FIGS. 1 and 2 illustrate, respectively, the growth kinetics and the kinetics of P-galactosidase activity of the three cultures.

The data given in FIG. 1 confirm the observation in Example 3: the three strains have comparable growth kinetics. The mutants of the ICONE line have, from this point of view, conserved the growth potential of E. coli RV308, and they thus remain potential candidates for industrial use.

The data in FIG. 2 show the impact of the mutations carried by the ICONE strains on the expression of the P-galactosidase in a fermenter. Clearly, on a glycerol-based medium, the presence or absence of the tryptophanase activity has no effect on the control of the expression, as attested thereto by the first part of the RV308 and ICONE 100 curves, even though it is observed that the exogenous tryptophan disappears more rapidly in the RV308 culture than in that of ICONE 100 (data not shown). On the other hand, the mutant ICONE 200 exhibits better capacities for controlling the expression at the start of culturing: the β-galactosidase activity remains low during the first 18 hours of culturing, and then begins to increase from t=20 h, the moment when the extracellular tryptophan concentration becomes zero (data not shown). The second part of the curve concerning ICONE 200 shows that the P-galactosidase activity increases evenly so as to reach a level at the end of culturing which is close to that obtained with RV308. In this respect, we demonstrate that the regulation system present in ICONE 200 provides a transient control of the plasmid Ptrp promoter. This control, exerted by the tryptophan and/or the carbon source, becomes ineffective in the second part of the culture and does not act against maximum expression of the recombinant protein.

EXAMPLE 5

Controlling the Expression of a Toxic Protein

This example describes the behavior of the strains RV308 and ICONE 200 in culture when they are transformed with a vector carrying, downstream of the tryptophan promoter, the gene of a toxic protein. By way of example, and so as to illustrate the invention, the gene of interest is the one encoding the poliovirus 2B protein. It has been described that the overexpression of this protein modifies the membrane permeability in bacteria (Lama et al., 1992) and in eukaryotic cells (Aldabe at al., 1996), which makes it a model of choice for studying the consequences of leaking of expression in *E. coli.*

The gene encoding the 2B protein is amplified from the vector pET3.2B (Lama et al., 1992) by a PCR reaction with the aid of the following oligonucleotides:

```
PO2.1         5'-GCGAATTCTGGCATCACCAATTACATAG-3'                       (SEQ ID NO. 23)
(sense)          EcoRI PO2.21        5'-GCAAGCTTAGTGGTGGTGGTGGTGGTGTTGCTTGATGACATAAGGTATC-3'  (SEQ ID NO. 24)
(antisense)      HindIII
```

The amplification product is then digested with the EcoRI and HindIII restriction enzymes, and then cloned into an expression vector which is derived from pBR322 and which carries the Ptrp tryptophan promoter. The resulting vector, named pVA-polio2B, carries a sequence encoding the 2B protein fused, at its C-terminal end, to a poly(His) tail, under the control of the Ptrp promoter. The vector pVA-polio23 is introduced into the *E. coli* RV308 and ICONE 200 bacteria by transformation. A recombinant clone of each construct is then cultured under conditions which are similar to those described in Example 4.

The growth kinetics of the RV308 and ICONE 200 bacteria measured by the optical density at 580 nm are given in FIG. 3. It appears clearly therein that RV308 exhibits a considerable growth delay: the mean generation time in the fermenter during the first 14 hours of culturing is 1 h 45 min, against only 1 h 17 min for ICONE 200. After culturing for 24 hours, the optical density for the strain RV308 is only equal to 13. Surprisingly, the strain ICONE 200 itself reaches an optical density equal to 37 after 17 h 30 min. of culturing, the time at which the induction is carried out by adding indole acrylic acid (IAA) at 25 $\mu$g/ml. The effect of the induction is immediate: the rate of oxygen consumption falls abruptly (data not shown) and growth stops.

Samples were taken at various culture times, god and analyzed for their recombinant protein content. Samples of biomass centrifuged at 8000 g are taken up in a P1 buffer (25 mM Tris, 1.15 mM EDTA, 1 mg/ml lysozyme, pH 8) in a proportion of 5 ml per 1 g of biomass. The biomass is resuspended, incubated for 15 min. at room temperature, and then subjected to a sonication for 2 min. The lyzate is centrifuged again (10 000 g, 15 min., 4° C.) so as to give a soluble fraction (supernatant) and an insoluble fraction (pellet taken up in 200 $\mu$l of P2 buffer: 25 mM Tris, 1 mM EDTA, pH 8). These samples are loaded onto polyacrylamide gel and subjected to an electrophoresis under denaturing conditions (SDS-PAGE). The gel is then transferred onto membrane according to the Western-blot technique in order to reveal the presence of the recombinant protein. The antibody used is a peroxidase-coupled anti-poly(His) monoclonal (Sigma). The revelation is performed by chemiluminescence with the ECL+kit (Amersham). FIGS. 4A and 4B give the result of the immunoblots on the insoluble fractions derived from the RV308 and ICONE 200 cultures, respectively. FIG. 4A shows that the recombinant protein is present in all the samples, i.e. from the start of culturing until the fermentation time t 24 h, even though no induction with IAA has been carried out. Conversely, with ICONE 200, no recombinant protein is detected before induction (FIG. 4B). It is only after induction with IAA that the 2B protein is detectable (in the insoluble fraction) and that the manifestation of its toxic nature is observed. Thus, these results demonstrate that the mutant ICONE 200 has a clear advantage with respect to the strain RV308 from which it is derived, and makes it possible to produce an effective control of expression in a fermenter.

EXAMPLE 6

Production of a toxic protein

This example is directed toward demonstrating that a toxic protein can be expressed in a culture of ICONE 200 *E. coli* at high cell density and under culture conditions which are suitable for industrial extrapolation. For this purpose, the ICONE 200 *E. coli* strain transformed with the vector pVA-polio 2B is evaluated. The results obtained in Example 5 indicate that the induction conditions must be optimized if instantaneous growth arrest and then bacterial lysis, caused by the expression, are to be avoided. Thus, this example describes various assays intended to optimize the yield of recombinant protein per unit of fermented volume by adjusting the inducer concentration and the cell density at induction. The culture conditions used are those described in Example 4.

The experimental combinations tested are as follows:

Experiment No. 1: induction with 25 $\mu$g/ml of IAA when the optical density is between 30 and 35;

Experiment No. 2: induction with 5 $\mu$g/ml of IAA when the optical density is between 30 and 35;

Experiment No. 3: induction with 25 $\mu$g/ml of IAA when the optical density is between 60 and 65;

Experiment No. 4: induction with 5 $\mu$g/ml of IAA when the optical density is between 60 and 65.

For each experiment, samples of biomass are removed at various times after induction and analyzed according to the following protocol. Approximately 20 grams of biomass are taken up in 100 ml of 1×Start Buffer (prepared from the 8× concentrate: 1.42 g $Na_2HPO_42H_{20}$, 1.11 g $NaH_2PO_4H_2O$, 23.38 g NaCl, q.s. 100 ml, pH 7.4). The suspension is treated by sonication for 3×5 min, and then centrifuged for 30 min at 20 000 g and 4° C. The pellet is taken up in 15 ml of Start Buffer+6 M guanidine-HCl +0.1% SB3-14 (N-tetradecyl-N, N-dimethyl-3-ammonio-1-propanesulfonate, Sigma), and then incubated in ice for 1 hour. The suspension is centrifuged for 1 hour at 30 000 g and 4° C. The supernatant is filtered through 0.45 $\mu$ with a view to purifying it by chelated-metal affinity chromatography. A column containing 1 ml of gel (HiTrap Chelating, Amersham Pharmacia Biotech) is loaded with 1 ml of 0.1 M $NiSO_4$, washed with 5 ml of water, and then equilibrated with 30 ml of Start Buffer +6 M guanidine-HCl +0.1% SB3-14. The sample is then loaded onto the column. A rinse with 60 ml of wash buffer (Start Buffer+6 M guanidine-HCl +0.1% SB3-14 +20 mM imidazole) makes it possible to eliminate the majority of the proteins bound via nonspecific interactions. The recombinant polio-2B protein is eluted with 10×1 ml of elution buffer (Start Buffer+6 M guanidine-HCl +0.1% SB3-14 +300 mM imidazole). The fractions with the highest protein concentrations are pooled and then desalified on Sephadex G-25 gel (PD10 columns, Amersham Pharmacia Biotech). The quality and quantity of polio-2B protein thus obtained are estimated by electrophoresis under denaturating conditions (SDS-PAGE) and by assaying total proteins (BCA method, Pierce), respectively.

FIG. 5 shows a Coomassie blue-stained SDS gel of the polio-2B proteins extracted and purified subsequent to experiments 1 to 4 described above. The size of the recombinant protein corresponds to the theoretical size (11 kDa) predicted from its coding sequence. In addition, it corresponds to the size of the major protein observed on a Western blot after induction, in the ICONE 200 *E. coli*× pVApolio-2B lyzate (FIG. 4B). It is thus probable that the proteins visible in FIG. 5 correspond to the poliovirus 2B protein fused to a polyhistidine tail. Moreover, the quality of the proteins obtained is identical under all the induction conditions tested.

Table 3 below summarizes the results obtained by combining various factors such as optical density at induction, inducer concentration and culture time after induction.

TABLE 3

Influence of the optical density at induction, of the inducer concentration and of the time after induction on the yield of expression of a toxic protein (example of polio-2B)

| Experiment No. | Optical density (580 nm) of the culture at the moment of induction | Inducer concentration (mg/l IAA) | Time after induction (HH:MM) | Quantity of protein extracted and purified (mg per liter of medium) |
|---|---|---|---|---|
| 1 | 32.5 | 25 | 00:45 | 3 |
| | | | 01:45 | 2 |
| 2 | 32.5 | 5 | 00:45 | 6 |
| | | | 01:45 | 6 |
| 3 | 62.5 | 25 | 00:45 | 5.5 |
| | | | 02:45 | 7.5 |
| 4 | 63.5 | 5 | 00:45 | 6 |
| | | | 02:50 | 9 |

In comparing the groups of experiments (1–2) and (3–4), it is observed that the later the induction is carried out, the higher the yield of expression. This confirms the advantage of growing the biomass as much as possible before triggering the induction. In the case of experiments (3–4), approximately 70% of the carbon substrate is consumed at the moment at which the expression of the polio-2B protein is triggered. With a strain such as ICONE 200, the cell growth phase and the expression phase are totally separated, which makes it possible to optimize the yield of recombinant protein, even when this protein is toxic.

In parallel with the induction time, the inducer concentration is also an influencing parameter. The best result of expression obtained in this example corresponds to experiment No. 4, in which the inducer concentration related to the number of cells is the lowest (5 mg/l of IAA for a culture with an optical density equal to 63.5). It is also in this experiment that the toxic effect of the expression of polio-2B is the least noticeable, since the culture continues to develop after induction, whereas growth is completely stopped in all the other experiments (see FIG. 6). It is thus particularly important to adjust the conditions for induction of a toxic protein in such a way as to find the optimum between an inducer concentration which is too low to give rise to a significant expression and a concentration which is too high, provoking the immediate arrest of the bacterial metabolism. In comparing the results of experiments No. 4 and No. 1, it is observed that an induction which is later (OD=63.5 against 32.5) and less strong (IAA concentration equal to 5 mg/l against 25 mg/l) makes it possible to multiply by 3- to 4-fold the quantity of recombinant protein obtained per unit of fermented volume.

The ICONE 200 *E. coli* strain, obtained by genetic modification according to the invention of a strain of industrial value, makes it possible to strictly control the expression of any gene placed in a plasmid vector downstream of the Ptrp tryptophan promoter. This control is transient since it is mediated by the exogenous tryptophan provided in the culture. The Ptrp induction potential in ICONE 200 is conserved, and remains possible to modulate via the IAA concentration. Due to these properties, ICONE 200 allows the controlled expression of recombinant proteins under culture conditions which can be extrapolated to large scale.

Bibliography Aldabe, R., Barco, A. & Carrasco, L., (1996). The Journal of Biological Chemistry 271, 23134–23137. Botsford, J. L. & DeMoss, R. D. (1971). Catabolite repression of tryptophanase in *Escherichia coli*. Journal of Bacteriology, 105, 303–312. Deeley, M. C.& Yanofsky, C. (1981). Nucleotide sequence of the structural gene for tryptophanase of *Escherichia coli* K-12. Journal of Bacteriology, 147, 787–796. Gunsalus, R. P., Yanofsky, C. (1980). Nucleotide sequence and expression of *E. coli* trpR, the structural gene for the trp aporepressor. Proceeding of the National Academy os Sciences, USA, 77, 12, 7117–7121. Gunsalus, R. P., Gunsalus Miguel, A. & Gunsalus, G. L. !31 (1986). Intracellular Trp repressor levels in *Escherichia coli*. Journal of Bacteriology, 167, 272–278. Hamilton, C. M., Aldea, M., Washburn, B. K., Babitzke, P. & Kushner, S. R. (1989). New method for generating deletions and gene replacements in *Escherichia coli*. Journal of Bacteriology, 171, 4617–4622.

Hasan, N. & Szybalski, W. (1995). Construction of lacIts and lacIqts expression plasmids and evaluation of the thermosensitive lac repressor. Gene, 163, 35–40. Hultman, T., Stahl, S., Hornes, E. & Uhlen, M. (1989). Direct solid phase sequencing of genomic and plasmid DNA using magnetic beads as solid support. Nucleic Acids Research, 17, 4937–4946. Issacs, H., Chao, D., Yanofsky, C. & Saier, M. H. (1994). Mechanism of catabolite repression of tryptophanase synthesis in *Escherichia coli*. Microbiology, 140, 2125–2134. Kelley, R. L. & Yanofsky, C. (1982) trp aporepressor production is controlled by autogenous regulation and inefficient translation. Proceedings of the National Academy of Sciences, USA, 79, 3120–3124. Lama, J. & Carrasco, L. (1992). The Journal of Biological Chemistry 267, 15932–15937.

What is claimed is:

1. Method for producing a recombinant protein wherein a gene encoding the protein is placed under the control of the Ptrp trytophan operon promoter, wherein the method comprises the following steps:

a) transforming a prokaryotic cell with a vector containing a nucleic acid sequence which is capable of inactivating the gene encoding a TnaA tryptophanase when said nucleic acid sequence is introduced into said host cell, and integrating said sequence into the DNA of said host cell; and before-hand, subsequently or simultaneously, introducing into said prokaryotic cell all or part of the sequence of a promoter which is followed, in the 3' position, by a nucleic acid sequence encoding a molecule which is ribonucleotide or protein in nature, and which acts negatively on the Ptrp promoter or its transcription product;

b) transforming said prokaryotic cell with a vector containing a gene encoding said recombinant protein;

c) culturing said transformed cell in a culture medium which allows the expression of the recombinant protein; and d) recovering the recombinant protein from the culture medium or from said transformed cell.

2. Method for producing a recombinant protein of claim 1, in which the nucleic acid sequence which is capable of inactivating the gene encoding a TnaA tryptophanase is introduced into the DNA of the prokaryotic host cell.

3. Method for producing the recombinant protein of claim 1 in which said nucleic acid sequence introduced into said host cell is introduced without any other DNA element which would allow a selective advantage to be associated therewith.

4. Method for producing a recombinant protein of claim 1 in which said nucleic acid introduced into said host cell is introduced at the tryptophanase operon locus.

5. Method for producing a recombinant protein of claim 1 wherein said method also comprises, between step a) and b), a resolution and a screening step.

6. Method for producing a recombinant protein of claim 1, in which the induction of said promoter which is followed, in the 3' position, by a nucleic acid sequence encoding a molecule which is ribonucleotide or protein in nature and which acts negatively on the Ptrp promoter or its transcription product is obtained by exerting on said promoter an inhibiting or activating effect.

7. Production method claim 6, in which the induction of said promoter which is followed, in the 3' position, by a nucleic acid sequence encoding a molecule which is ribonucleotide or protein in nature, and which acts negatively on the Ptrp promoter or its transcription product is obtained either:

a) by choosing a suitable carbon source in the culture medium; or b) by adding tryptophan to the culture medium; or c) by a combination of a) and b).

8. Method of claim 1 wherein the prokaryotic host cell is a Gram-negative bacterium.

9. Method of claim 8, wherein the prokaryotic host cell is E. coli.

10. A first construct for transforming a prokaryotic host cell which can be transformed with a second construct for expressing a gene encoding a recombinant protein placed under the control of a Ptrp tryptophan operon promoter in a prokaryotic host cell, wherein the first construct comprises a nucleic acid sequence which is capable of inactivating the gene encoding a TnaA tryptophanase when said nucleic acid sequence is introduced into said host cell.

11. The first construct of claim 10, wherein it also comprises, upstream of said nucleic acid sequence capable of inactivating the gene encoding a TnaA tryptophanase when said nucleic acid sequence is introduced into said host cell, all or part of the nucleic acid sequence of a Ptna tryptophanase operon promoter.

12. The first construct of claim 10, wherein said nucleic acid sequence capable of inactivating the gene encoding a TnaA tryptophanase when said nucleic acid sequence is introduced into said host cell comprises a mutated fragment of the coding sequence of said TnaA tryptophanase.

13. The first construct of claim 12, wherein said mutated fragment is obtained by inserting a stop codon at a position such that the sequence of the mutated fragment thus obtained encodes a protein fragment lacking tryptophanase activity.

14. The first construct of claim 12, wherein said mutated fragment is a mutated fragment of the coding sequence of the TnaA tryptophanase of said host cell.

15. The first construct of claim 10, wherein said nucleic acid sequence capable of inactivating the gene encoding a TnaA tryptophanase when said nucleic acid sequence is introduced into said host cell is the nucleic acid sequence comprising all or part of the sequence of a promoter followed, in the 3' position, by a nucleic acid sequence encoding a molecule which is ribonucleotide or protein in nature, and which acts negatively on the Ptrp promoter or its transcription product.

16. The first construct of claim 15, wherein said promoter followed, in the 3' position, by a nucleic acid sequence encoding a molecule which is ribonucleotide or protein in nature, and which acts negatively on the Ptrp promoter, is all, or a part permitting promoter activity, of the Ptna tryptophanase operon promoter.

17. The first construct of claim 16, wherein said nucleic acid sequence encoding a molecule which is ribonucleotide or protein in nature, and which acts negatively on the Ptrp promoter, is the sequence encoding the TrpR tryptophan operon aporepressor or the biologically active fragment obtained by amplification of the coding sequence of the TrpR gene using the pair of primers having the sequences TrpR3 (SEQ ID No. 17) and TrpR4 (SEQ ID No. 18).

18. Vector containing a first construct of claim 10.

19. Vector of claim 18, wherein it is the vector pMAK705 [tnaAt]or the vector pMAK705 [Ptna:trpR:3'tna].

20. Prokaryotic host cell transformed with a vector of claim 18.

21. Prokaryotic host cell of claim 20, wherein it is *E. coli*.

\* \* \* \* \*

UNITED STATES PATENT AND TRADEMARK OFFICE
CERTIFICATE OF CORRECTION

PATENT NO. : 6,844,169 B1 Page 1 of 1
APPLICATION NO. : 09/673288
DATED : January 18, 2005
INVENTOR(S) : Laurent Chevalet et al.

It is certified that error appears in the above-identified patent and that said Letters Patent is hereby corrected as shown below:

Cover Page, item (74):  "Mueschen" should be --Hueschen--.

Signed and Sealed this

Thirty-first Day of March, 2009

JOHN DOLL
*Acting Director of the United States Patent and Trademark Office*

SEQUENCE LISTING

<160> NUMBER OF SEQ ID NOS: 24

<210> SEQ ID NO 1
<211> LENGTH: 30
<212> TYPE: RNA
<213> ORGANISM: Escherichia coli

<400> SEQUENCE: 1
auucgcgucu acggcuucau cguguugcgc                                         30

<210> SEQ ID NO 2
<211> LENGTH: 93
<212> TYPE: RNA
<213> ORGANISM: Escherichia coli

<400> SEQUENCE: 2
auucgcgucu acggcuucau cguguugcgc agcacaacgc gccugucacc ggauguguuu       60
uccggucuga ugaguccgug aggacgaaac agg                                    93

<210> SEQ ID NO 3
<211> LENGTH: 53
<212> TYPE: RNA
<213> ORGANISM: Escherichia coli

<400> SEQUENCE: 3
auucaguacg aaaauugcuu ucauaauucu agauacccuu uuuacgugaa cuu              53

<210> SEQ ID NO 4
<211> LENGTH: 116
<212> TYPE: RNA
<213> ORGANISM: Escherichia coli

<400> SEQUENCE: 4
auucaguacg aaaauugcuu ucauaauucu agauacccuu uuuacgugaa cuuagcacaa       60
cgcgccuguc accggaugug uuuuccgguc ugaugagucc gugaggacga aacagg          116

<210> SEQ ID NO 5
<211> LENGTH: 83
<212> TYPE: RNA
<213> ORGANISM: Escherichia coli

<400> SEQUENCE: 5
auucgcgucu acggcuucau cguguugcgc auucaguacg aaaauugcuu ucauaauucu       60
agauacccuu uuuacgugaa cuu                                               83

<210> SEQ ID NO 6
<211> LENGTH: 146
<212> TYPE: RNA
<213> ORGANISM: Escherichia coli

<400> SEQUENCE: 6
auucgcgucu acggcuucau cguguugcgc auucaguacg aaaauugcuu ucauaauucu       60
agauacccuu uuuacgugaa cuuagcacaa cgcgccuguc accggaugug uuuuccgguc      120
ugaugagucc gugaggacga aacagg                                           146

<210> SEQ ID NO 7
<211> LENGTH: 40
<212> TYPE: RNA
<213> ORGANISM: Escherichia coli

```
<400> SEQUENCE: 7
cuucgcgucc ugaugagucc gugaggacga aacggcuucc                           40

<210> SEQ ID NO 8
<211> LENGTH: 103
<212> TYPE: RNA
<213> ORGANISM: Escherichia coli

<400> SEQUENCE: 8
cuucgcgucc ugaugagucc gugaggacga aacggcuucc agcacaacgc gccugucacc    60
ggauguguuu uccggucuga ugaguccgug aggacgaaac agg                      103

<210> SEQ ID NO 9
<211> LENGTH: 27
<212> TYPE: DNA
<213> ORGANISM: Escherichia coli

<400> SEQUENCE: 9
cgggatccgt gtgacctcaa aatggtt                                        27

<210> SEQ ID NO 10
<211> LENGTH: 30
<212> TYPE: DNA
<213> ORGANISM: Escherichia coli

<400> SEQUENCE: 10
ctacgcgccg ctgcttcgga ttagatctcg                                     30

<210> SEQ ID NO 11
<211> LENGTH: 27
<212> TYPE: DNA
<213> ORGANISM: Escherichia coli

<400> SEQUENCE: 11
cgtctagaca gcggcagtcg tagctac                                        27

<210> SEQ ID NO 12
<211> LENGTH: 27
<212> TYPE: DNA
<213> ORGANISM: Escherichia coli

<400> SEQUENCE: 12
ccttctctaa ccgcaacagt tcgaacg                                        27

<210> SEQ ID NO 13
<211> LENGTH: 19
<212> TYPE: DNA
<213> ORGANISM: Escherichia coli

<400> SEQUENCE: 13
cgacgaagcc taatctaga                                                 19

<210> SEQ ID NO 14
<211> LENGTH: 19
<212> TYPE: DNA
<213> ORGANISM: Escherichia coli

<400> SEQUENCE: 14
ccgatattcc tacaatcgg                                                 19

<210> SEQ ID NO 15
```

-continued

```
<210> SEQ ID NO 15
<211> LENGTH: 26
<212> TYPE: DNA
<213> ORGANISM: Escherichia coli

<400> SEQUENCE: 15
ctggatccct gtcagatgcg cttcgc                                              26

<210> SEQ ID NO 16
<211> LENGTH: 23
<212> TYPE: DNA
<213> ORGANISM: Escherichia coli

<400> SEQUENCE: 16
cttcctaata cattaccggg ttg                                                 23

<210> SEQ ID NO 17
<211> LENGTH: 20
<212> TYPE: DNA
<213> ORGANISM: Escherichia coli

<400> SEQUENCE: 17
gtaatggccc aacaatcacc                                                     20

<210> SEQ ID NO 18
<211> LENGTH: 29
<212> TYPE: DNA
<213> ORGANISM: Escherichia coli

<400> SEQUENCE: 18
cacaacgact tttcgctaac tgacgtcag                                           29

<210> SEQ ID NO 19
<211> LENGTH: 25
<212> TYPE: DNA
<213> ORGANISM: Escherichia coli

<400> SEQUENCE: 19
cgctgcagtt aatactacag agtgg                                               25

<210> SEQ ID NO 20
<211> LENGTH: 24
<212> TYPE: DNA
<213> ORGANISM: Escherichia coli

<400> SEQUENCE: 20
ccagctaatg aggtaagttc gaac                                                24

<210> SEQ ID NO 21
<211> LENGTH: 20
<212> TYPE: DNA
<213> ORGANISM: Escherichia coli

<400> SEQUENCE: 21
gggcaggtga actgctggcg                                                     20

<210> SEQ ID NO 22
<211> LENGTH: 22
<212> TYPE: DNA
<213> ORGANISM: Escherichia coli

<400> SEQUENCE: 22
ggtgccgtta taagggtcgg ac                                                  22
```

-continued

```
<210> SEQ ID NO 23
<211> LENGTH: 28
<212> TYPE: DNA
<213> ORGANISM: Escherichia coli

<400> SEQUENCE: 23
gcgaattctg gcatcaccaa ttacatag                                            28

<210> SEQ ID NO 24
<211> LENGTH: 43
<212> TYPE: DNA
<213> ORGANISM: Escherichia coli

<400> SEQUENCE: 24
gcaagcttag tggtggtggt ggtggtgttg cttgatgaca taa                            43
```